United States Patent [19]
Hansen

[11] Patent Number: 5,690,687
[45] Date of Patent: Nov. 25, 1997

[54] PACEMAKER WITH IMPROVED DISTRIBUTED RATE PACING

[75] Inventor: James C. Hansen, Denver, Colo.

[73] Assignee: Pacesetter, Inc., Sylmar, Calif.

[21] Appl. No.: 701,386

[22] Filed: Aug. 22, 1996

[51] Int. Cl.$^6$ ........................................... A61N 1/36
[52] U.S. Cl. .................................................. 607/17
[58] Field of Search ........................ 607/17, 18, 19, 607/20, 21, 22, 23

[56] References Cited

U.S. PATENT DOCUMENTS

4,856,522  8/1989  Hansen.
5,431,689  7/1995  Weinberg et al. ................. 607/14
5,441,523  8/1995  Nappholz.
5,514,162  5/1996  Bornzin et al. ................... 607/19

Primary Examiner—Scott M. Getzow
Attorney, Agent, or Firm—Gottlieb, Rackman & Reisman

[57] ABSTRACT

A rate responsive pacemaker generates an initial histogram of a rate control parameter. The histogram is then normalized to conform to preselected characteristics. For example. By linearizing a portion of the histogram. The new histogram is used to map the parameter into a corresponding pacing rate.

17 Claims, 7 Drawing Sheets

PACEMAKER WITH IMPROVED DISTRIBUTED RATE PACING

BACKGROUND OF THE INVENTION

A. Field of the Invention

This invention relates to single or dual chamber pacemakers, and more particularly to a mode of operation wherein intrinsic cardiac activity in one or more cardiac chambers are monitored and if no intrinsic activity is sensed then, after a preset duration, the chamber is paced. Importantly, in the absence of intrinsic beats, the pacing rate is determined from a metabolic demand parameter, using the past statistic history of the patient and other information derived from the general population.

B. Description of the Prior Art

Conventional pacemakers operating, for example, in a DDDX mode are normally provided with means for sensing and pacing both the atrium and the ventricle. In may of these types of pacemakers, the pacing rate is determined from a metabolic demand parameter, such as, for example the minute volume. A pacemaker of this type is described for example, in U.S. Pat. No. 5,441,523, incorporated herein by reference.

A disadvantage of these types of pacemakers is that, because the metabolic demand parameter is dependant on a number of factors, such as stress, chemical balance, athletic activity and so forth, it is difficult to derive an accurate mapping for converting an instantaneous metabolic parameter to a corresponding pacing rate. This task is made more difficult by the fact that the mapping has to adapt for various changes in the patient, due for example to changes in physician fitness, age and so on.

A solution to this problem has been offered in commonly assigned U.S. Pat. No. 4,856,522, incorporated herein by reference, and commonly referred to as a rate distributed pacemaker. In this patent, a statistical approach is developed as follows. First, a desired probability distribution function for the patient is set and used to calculate a corresponding rate percentile ranking. Next, a probability distribution function for the selected control parameter (such as the metabolic demand) is accumulated from the patient over an extended time period, and a corresponding percentile ranking for the parameter is calculated. Thereafter, for each instantaneous metabolic demand, the two percentile rankings are correlated and used to determine a corresponding pacing rate. While this approach has a number of advantages, it may not be ideal because it generates arbitrary functions which may or may not be correlated to functions developed and found acceptable by the experts in the field.

OBJECTIVES AND SUMMARY OF THE INVENTION

In view of the above-mentioned disadvantages of the prior art, it is an objective of the present invention to provide a rate distributed pacemaker in which the percentile ranking of the pacing rate is preselected in accordance with a desired function.

A further objective is to provide a rate distributed pacemaker in which the percentile rate of the control parameter is also preset in accordance with a preselected function derived from statistical data.

Other objectives and advantages of the invention shall become apparent from the following description. Briefly, a pacemaker constructed in accordance with this invention includes means for sensing cardiac activity of patient, means for generating pacing pulses on demand; means for sensing a metabolic demand parameter and deriving means for deriving a pacing rate for said pacing pulses based on said parameter, wherein said deriving means includes means for accumulating statistical data from said patient over an extended period and means for deriving percentile rankings of the parameter and the intrinsic beats in accordance with a preselected criteria.

Further objects, features and advantages of the invention will become apparent upon consideration of the following description, taken in conjunction with the accompanying drawings.

Briefly, a rate responsive pacemaker constructed in accordance with this invention includes a pulse generator for generating pacing pulses on demand in accordance with a control signal; and a controller including a histogram generator for generating an initial histogram for a rate control parameter, a normalizer for generating a normalized histogram from said initial histogram, said normalized histogram having predetermined characteristics, and a selector for selecting said rate control signal in accordance with said normalized histogram in response to an instantaneous rate control parameter. The initial histogram is generated from the rate control parameter over an extended time period, i.e. several days. This initial histogram is then normalized so that the normalized histogram has certain preselected characteristics. For example the histogram may be linear between certain limits or values of the rate control parameter. Similarly a histogram may be derived for the control rate based on statistical information available from the literature or by other means. This histogram is also normalized in accordance with preselected characteristics. The two normalized curves are used to map the rate control parameter into a control rate. Pacing pulses are then generated at the control rate on demand, i.e. in the absence of an intrinsic beat within a preselected escape period.

BRIEF DESCRIPTION OF THE DRAWINGS

FIG. 8b shows the integral of the curve of FIG. 8a;

FIG. 9a shows a typical MIR histogram;

FIG. 9b shows the integral of the curve of FIG. 9a; and

FIG. 9c shows the normalized curve obtained from the curve of FIG. 9b.

DETAILED DESCRIPTION OF THE INVENTION

Figure 1:
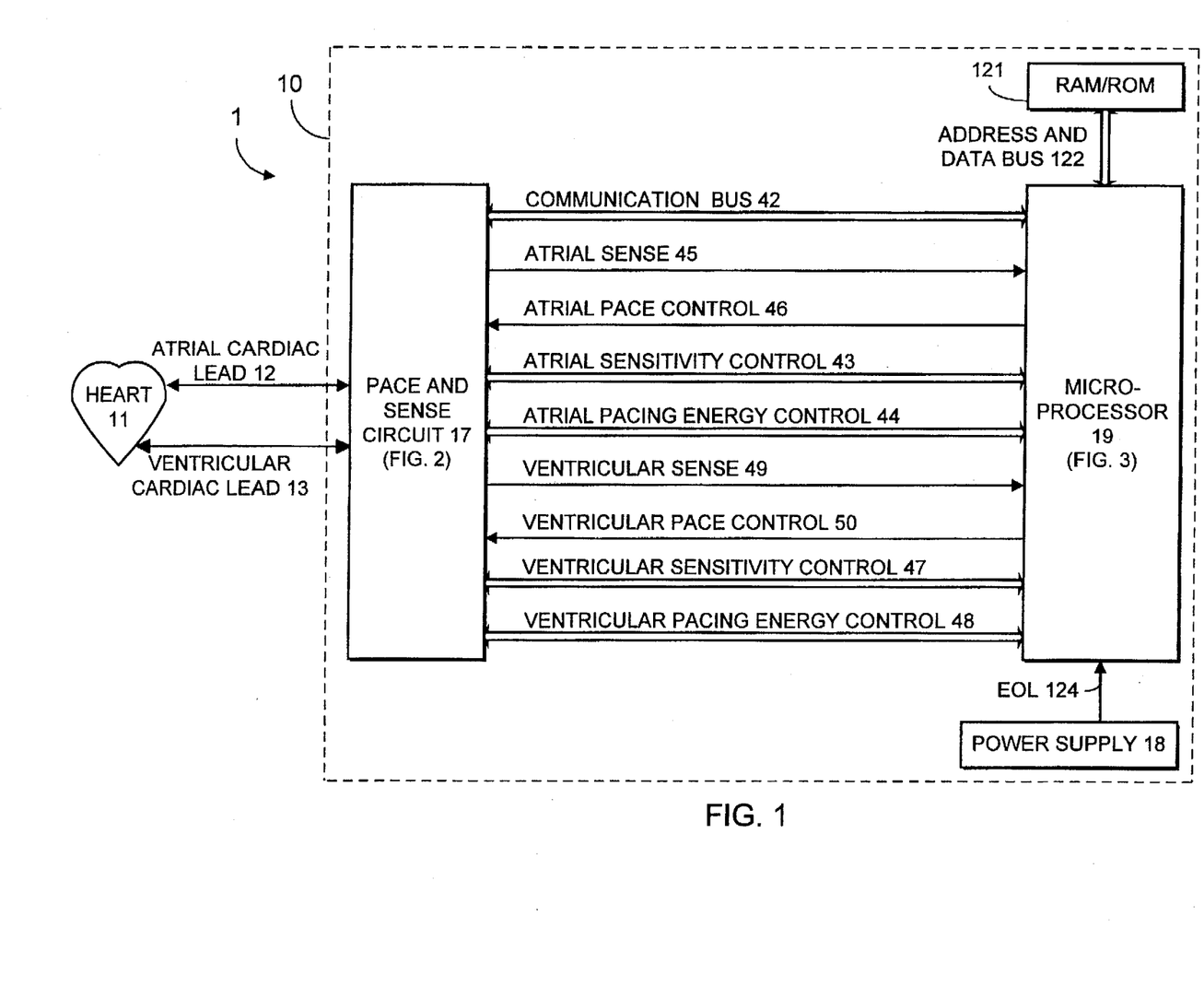
FIG. 1 is a block diagram of a rate-responsive, dual chamber pacemaker which embodies the subject invention.

FIG. 1 shows a block diagram of a pacemaker 1. The pacemaker 1 is designed to be implanted in a patient and includes a pulse generator 10 and appropriate leads for electrically connecting the pulse generator to a patient's heart 11. The pacemaker includes an atrial cardiac lead 12 extending to the atrium of the patient's heart for the administration of pacing therapy to the atrium, and a ventricular cardiac lead 13 extending to the ventricle of the patient's heart for the administration of pacing therapy to the ventricle. The pulse generator 10 includes a pace and sense circuit 17 for the detection of analog signals representing cardiac electrical activity and for the delivery of pacing pulses to the heart; a microprocessor 19 which, in response to numerous inputs received from the pace and sense circuit 17, performs operations to generate different control and data outputs to the pace and sense circuit 17; and a power supply 18 which provides a reliable voltage level to the pace and sense circuit 17 and the microprocessor 19 by electrical conductors (not shown).

The microprocessor 19 is connected to a random access memory/read only memory unit 121 by an address and data bus 122. An end-of-life signal line 124 is used to provide, to the microprocessor 19, a logic signal indicative of the approach of battery failure in the power supply 18. The microprocessor 19 and the pace and sense circuit 17 are connected by a communication bus 42, an atrial sense line 45, an atrial pacing control line 46, an atrial sensitivity control bus 43, an atrial pace energy control bus 44, a ventricular sense line 49, a ventricular pace control line 50, a ventricular sensitivity control bus 47, and a ventricular pacing energy control bus 48.

Figure 2:
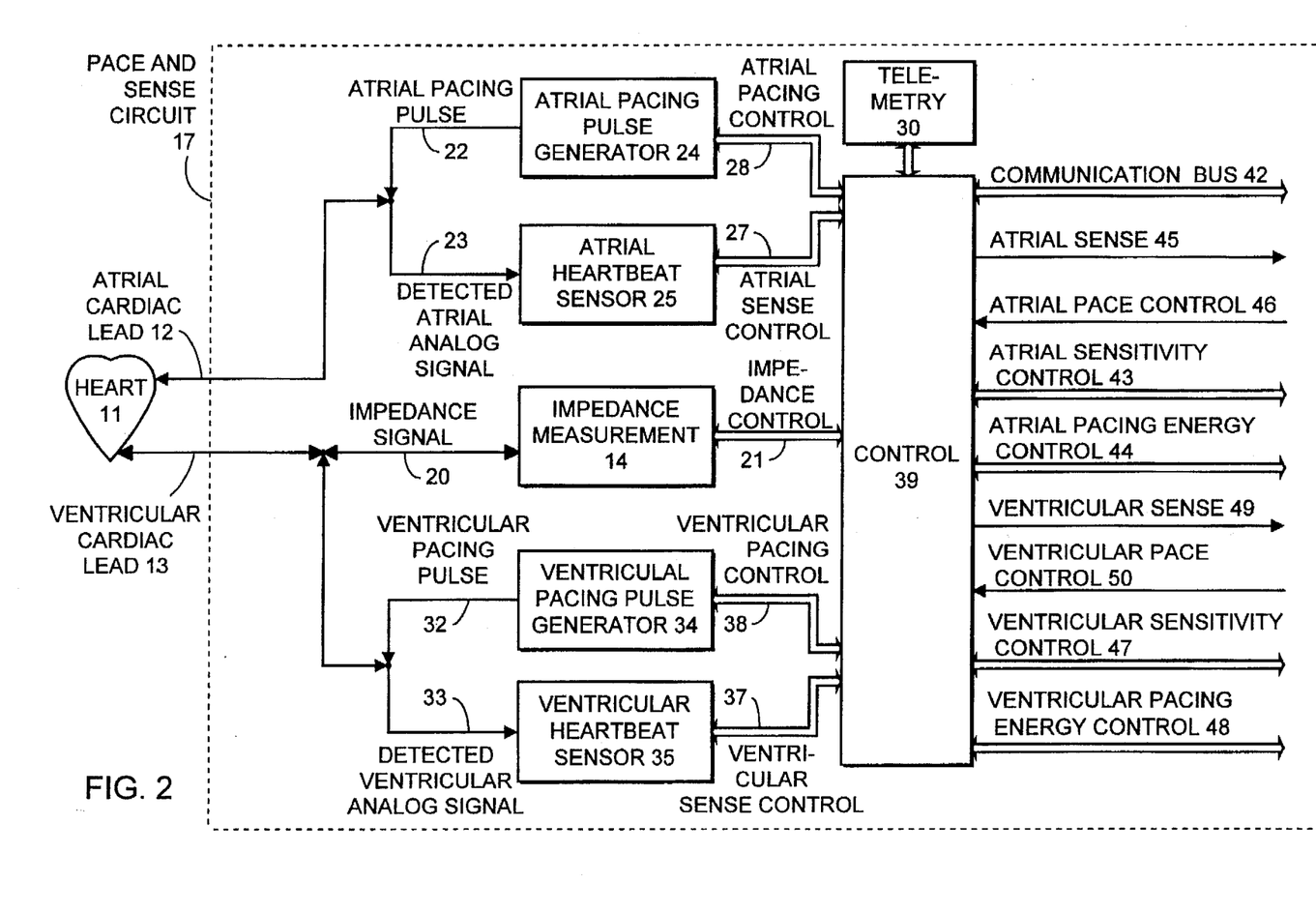
FIG. 2 is a block diagram of the pace and sense circuit for the pacemaker of FIG. 1.

FIG. 2 shows the pace and sense circuit 17 which includes circuitry for an atrial pacing pulse generator 24, a ventricular pacing pulse generator 34, an atrial heartbeat sensor 25, a ventricular heartbeat sensor 35, and a telemetry circuit 30. The preferred embodiment of the pace and sense circuit 17 includes an impedance measurement circuit 14 for measuring a physiological parameter indicative of the patient's metabolic demand. Also, the pace and sense circuit 17 includes a control block 39 which has an interface to the microprocessor 19.

In operation, the atrial and ventricular heartbeat sensor circuits 25 and 35 detect respective atrial and ventricular analog signals 23 and 33 from the heart 11 and convert the detected analog signals to digital signals. In addition, the heartbeat sensor circuits 25 and 35 receive an input atrial sense control 27 and an input ventricular sense control 37, respectively, from the control block 39 which determines the sensitivities of the sensor circuits. The sensitivity determines the minimum voltage deviation required at a sensing electrode for a sense to be registered, i.e., a depolarization signal to be recognized by the pacemaker.

The atrial pacing pulse generator circuit 24 receives from the control block 39, via an atrial pacing control bus 28, an atrial pace control input and an atrial pacing energy control input to generate an atrial pacing pulse 22 [A-pace] at appropriate times. Similarly, the ventricular pacing pulse generator circuit 34 receives from the control block 39, via a ventricular pacing control bus 38, a ventricular pace control input and a ventricular pacing energy control input to generate a ventricular pacing pulse [V-pace] 32. The atrial and ventricular pace control inputs determine the respective types of atrial and ventricular pacing that take place, while the atrial and ventricular pacing energy control inputs determine the respective magnitudes of the pulse energies.

The pacemaker 1 makes an impedance measurement when the microprocessor 19 sends a signal on the impedance control bus 21 to activate the impedance measurement circuit 14. The impedance measurement circuit 14 then applies a current to the ventricular cardiac lead 13 and measures a voltage resulting from the applied current to monitor the impedance. The current and voltage signals jointly are termed an impedance signal 20.

The telemetry circuit 30 provides a bidirectional link between the control block 39 of the pace and sense circuit 17 and an external device such as a programmer. It allows data such as the operating parameters to be read from or altered in the implanted pacemaker. An exemplary programmer is the 9600 Network Programmer manufactured by Telectronics Pacing Systems, Inc. of Englewood, Colo., U.S.A.

Figure 3:
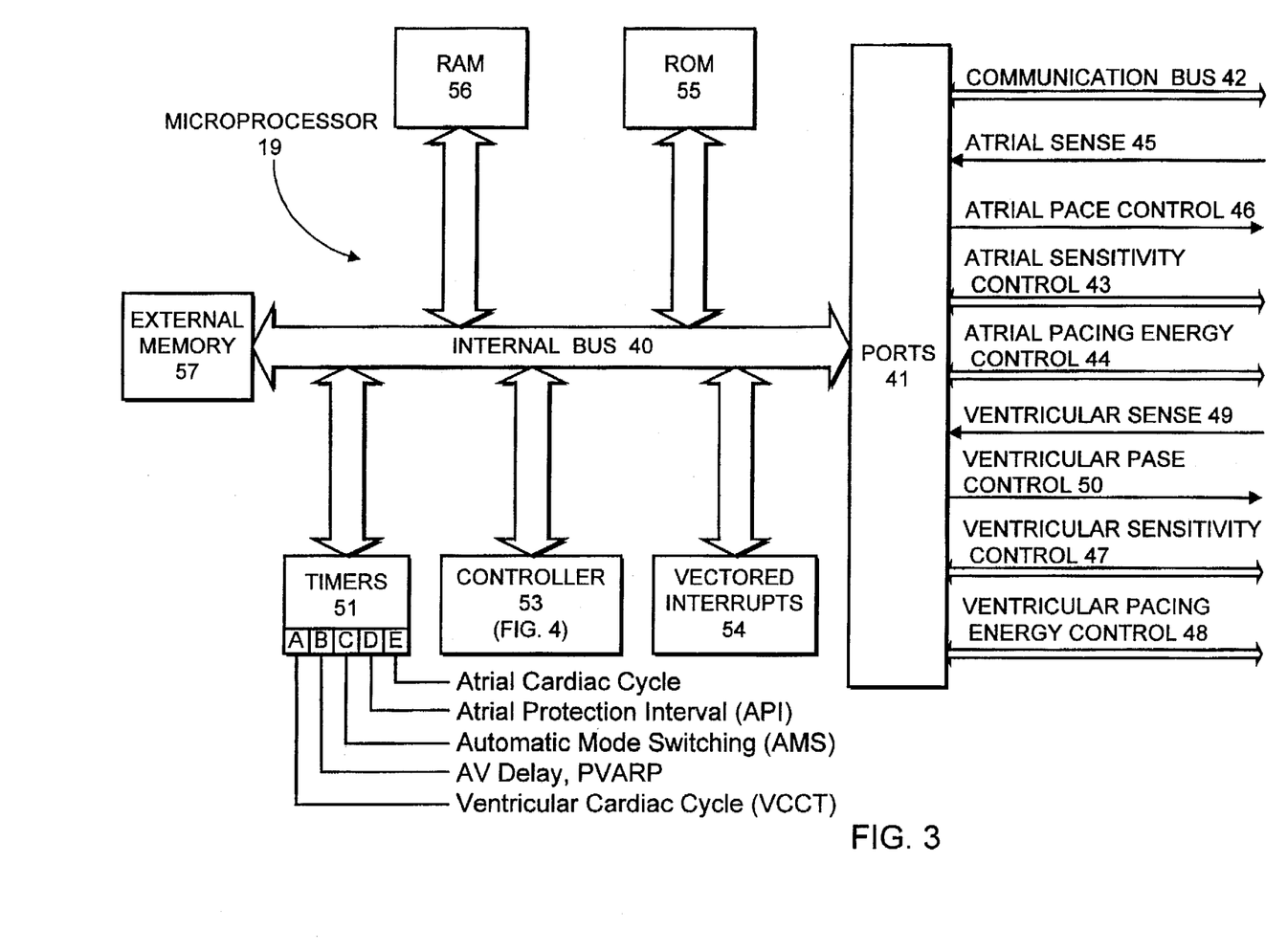
FIG. 3 is a block diagram of the microprocessor of FIG. 1.

FIG. 3 shows the microprocessor 19 as comprising a timer circuit 51 which may include multiple individual 16-bit timer circuits, a controller 53, a vectored interrupts block 54, a ROM 55, a RAM 56, an external memory 57 and a ports block 41. These circuits mutually communicate using an internal communications bus 40. In one embodiment of the invention, five timer circuits are required (for example, a ventricular cardiac cycle timer 51A, an AV delay and PVARP timer 51B, an automatic mode switching (AMS) timer 51C, an atrial protection interval (API) timer 51D and an atrial cardiac cycle timer 51E). Thus, the timer 51 may include five individual circuits or may include one or more timer circuits with a single timer performing multiple function timing operations (such as timer 51B) under direction of software running on the controller 53. The RAM 56 acts as a scratchpad and active memory during execution of the programs stored in the ROM 55 and used by the microprocessor 19. These programs include system supervisory programs, detection algorithms for detecting and confirming arrhythmias, and programming for implementing the logic diagram of FIGS. 12, 13, 14 and 15, as well as storage programs for storing, in external memory 57, data concerning the functioning of the pulse generator 10 and the electrogram provided by the ventricular cardiac lead 13. The timers 51, and their associated control software, implement some timing functions required by the microprocessor 19 without resort entirely to software, thus reducing computational loads on, and power dissipation by, the controller 53.

Signals received from the telemetry circuit 30 permit an external programmer (not shown) to change the operating parameters of the pace and sense circuit 17 by supplying appropriate signals to the control block 39. The communications bus 42 serves to provide signals indicative of such control to the microprocessor 19.

Appropriate telemetry commands will cause the telemetry circuit 30 to transmit data to the external programmer. Data stored is read out, by the microprocessor 19, on to the communications bus 42, through the control block 39 in the pace and sense circuit 17, and into the telemetry circuit 30 for transmission to the external programmer by a transmitter in the telemetry circuit 30.

The microprocessor 19 through its ports block 41 receives status and/or control inputs from the pace and sense circuit 17, such as the sense signals on the sense lines 45 and 49. It performs operations, including arrhythmia detection, and produces outputs, such as the atrial pace control on the line 46 and the ventricular pace control on the line 50, which determine the type of pacing that is to take place. Other control outputs generated by the microprocessor 19 include the atrial and ventricular pacing energy controls on the buses 44 and 48, respectively, which determine the magnitude of the pulse energy, and the atrial and ventricular sensitivity controls on the buses 43 and 47, respectively, which set the sensitivities of the sensing circuits.

The pacemaker 1 may employ a metabolic sensor to distinguish whether atrial heartbeats are occurring at a physiological rate or a pathological rate. The pacemaker 1 responds to a physiological atrial rate by functioning in an AV synchronous pacing mode with pacing pulses in the ventricle delivered a predetermined interval following an atrial heartbeat. When the pacemaker 1 detects a pathological atrial rate, it responds by functioning in the forced synchrony mode of operation. A metabolic sensor system, which is suitable for operation in the present invention, may be made up of one or more known sensors either solely or in combination with other sensors, including but not limited to minute volume, ventricular depolarization gradient, QT-interval, oxygen saturation, Ph, central venous blood temperature, right ventricular pressure, stroke volume, systolic time intervals, respiration rate and ultrasonic or pressure monitoring of cardiac output. The pacemaker 1 of the present invention will function properly using any metabolic indicator rate system, so long as that system is able to reliably relate the sensed parameter to a metabolic demand pacing rate. U.S. Pat. No. 4,766,901, to F. Callaghan, issued Aug. 30, 1988, for "Rate Responsive Pacing System Using the Integrated Evoked Potential," refers to the operation of a rate-responsive pacing system using an integrated evoked ventricle depolarization potential as a metabolic demand pacing rate indicator. U.S. Pat. No. 4,702,253 to T. Nappholz et al., issued Oct. 27, 1987, for "Metabolic-Demand Pacemaker and Method of Using the Same to Determine Minute Volume," and U.S. Pat. No. 4,901,725, to T. Nappholz et al., issued Feb. 20, 1990 for "Minute Volume Rate-Responsive Pacemaker", disclose rate-responsive pacers describing another metabolic demand pacing rate indicator, respiratory minute volume, as the rate control parameter. The above-mentioned patents are hereby incorporated by reference. The preferred embodiment of the invention employs an impedance sensor 14, shown in FIG. 2 which may perform the respiratory minute volume measurements of the Nappholz et al. patents.

Figure 4:
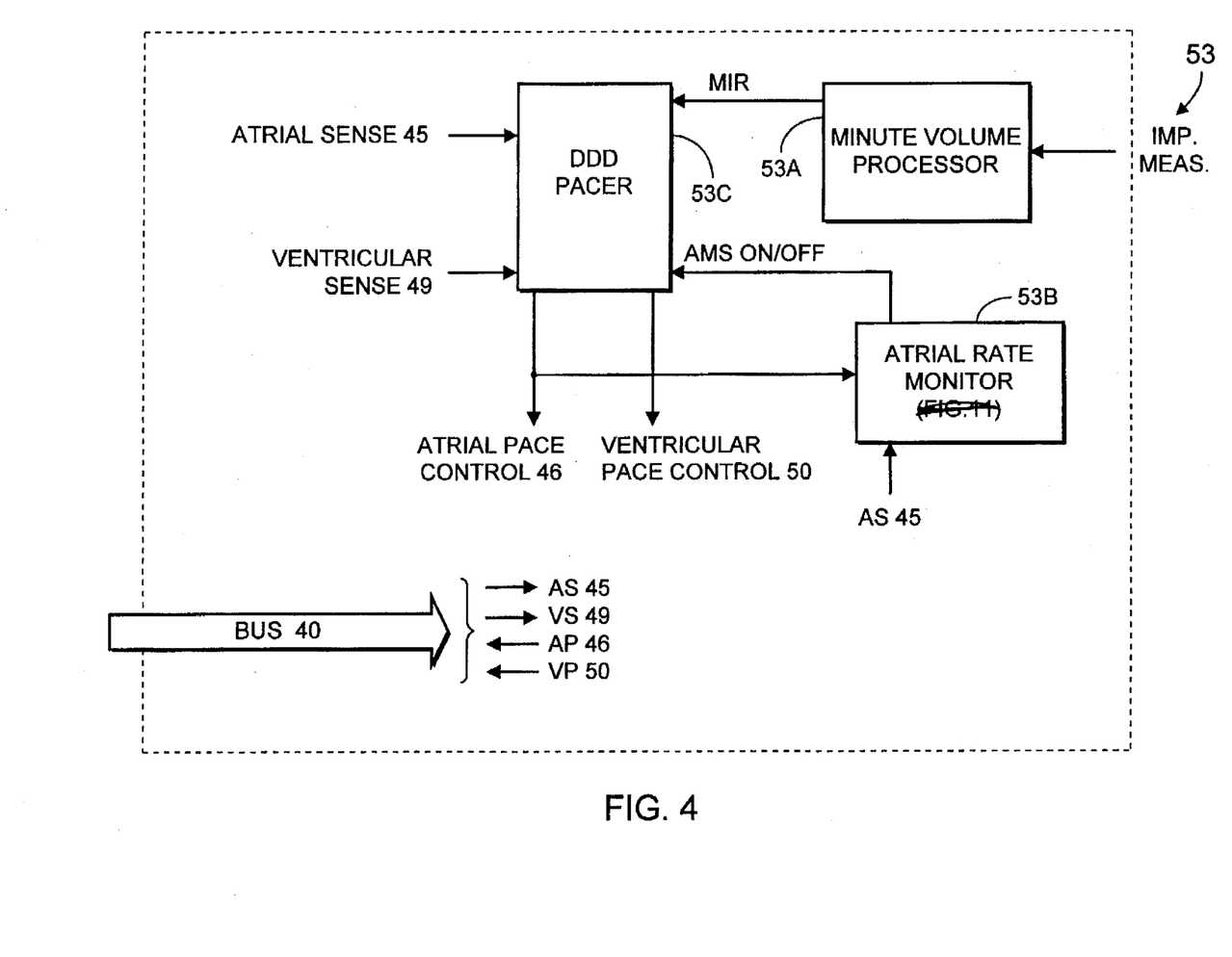
FIG. 4 is a functional block diagram of the controller of FIG. 3.

FIG. 4 shows the functional block diagram of the controller 53 of FIG. 3. The minute volume processor 53A uses the data supplied via the internal bus 40 and the communication bus 42 from the impedance measurement block 14 to generate the Metabolic Indicated Rate Interval [MIR] which is used by the pacing and sensing system (shown symbolically as the "DDD pacer block 53C in FIG. 4) to determine the length of each of the intervals used in the timing cycle. The atrial rate monitor 53B, whose functional block diagram is depicted in FIG. 11, generates an AMS signal which will be described at length below. FIG. 4 depicts the signals which control several of the operations involved in the forced synchrony sequencing.

Figure 5:
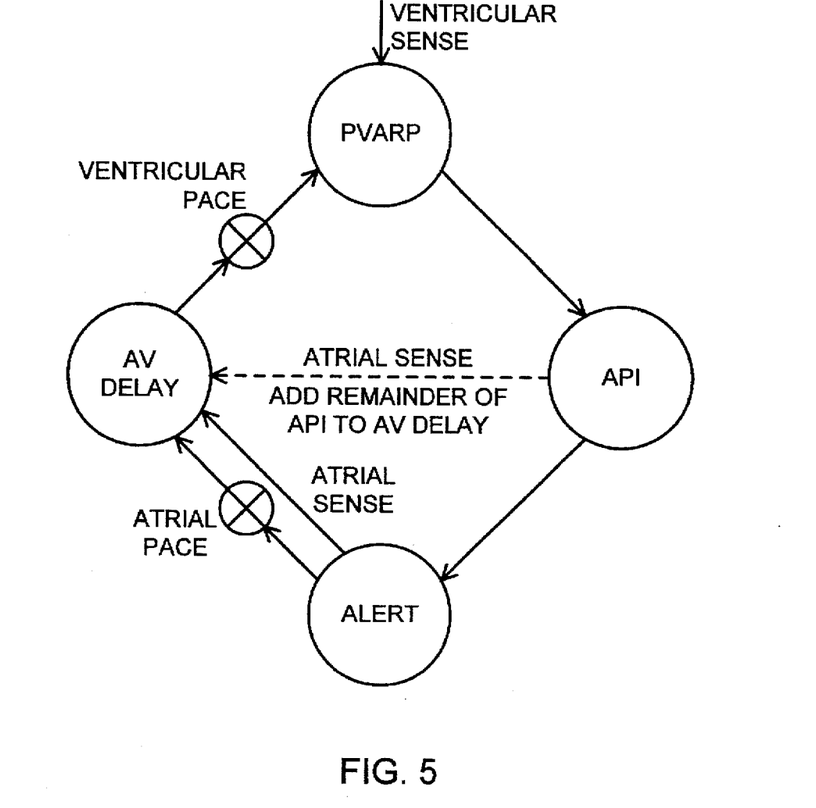
FIG. 5 is a state diagram that characterizes the operation of the pacemaker of FIG. 1.

The pacemaker state diagram is shown in FIG. 5. The PVARP is the Post Ventricular Atrial Refractory Period. An A-sense occurring during this interval is considered to be due to a retrogradely conducted ventricular event and is ignored. A V-sense occurring at any time starts the PVARP.

The API is the Atrial Protection Interval and defines the minimum time between an ignored A-sense (i.e., in the PVARP) and the next A-pace. The API is intended to prevent an A-pace being provided during the vulnerable part of the atrial repolarization period, i.e., the relative refractory period during which arrhythmias may be induced. For example, the API may be controlled to ensure that the sum of the AV delay, the PVARP and the Alert interval is less than 70% of the VV rate interval indicated by the MIR.

The Alert is the interval during which A-senses are classified to be P-waves (i.e., of sinus origin ) within the correct rate range. Such P-waves are tracked 1:1 by the ventricular channel. The Alert is the remainder of VV interval after the sum of the AV delay plus the PVARP plus the API.

Figure 6:
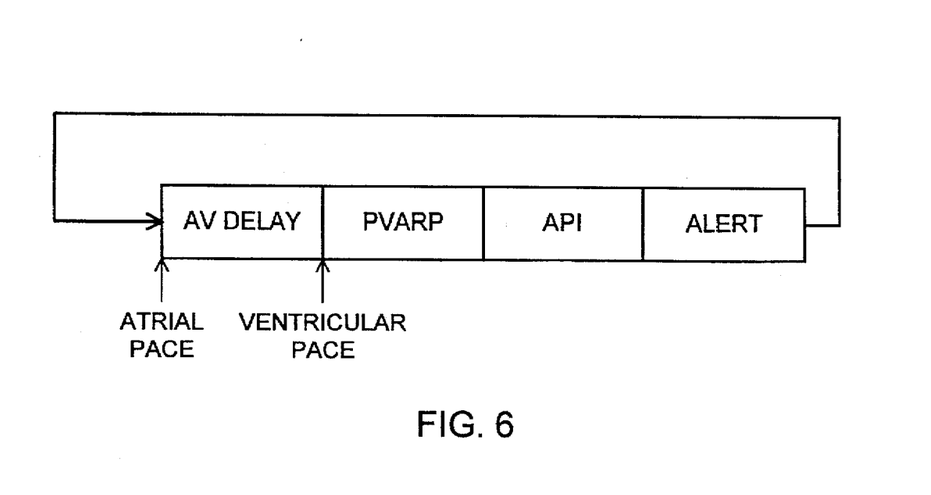
FIG. 6 shows a timing diagram with he various phases of a typical pacing cycle.

The AV delay is intended to mimic the natural P-wave to R-wave interval and is the time between an A-sense (or A-pace) and a V-pace (in the absence of a V-sense). The sequence of a typical pacing cycle is shown in FIG. 6.

Figure 7:
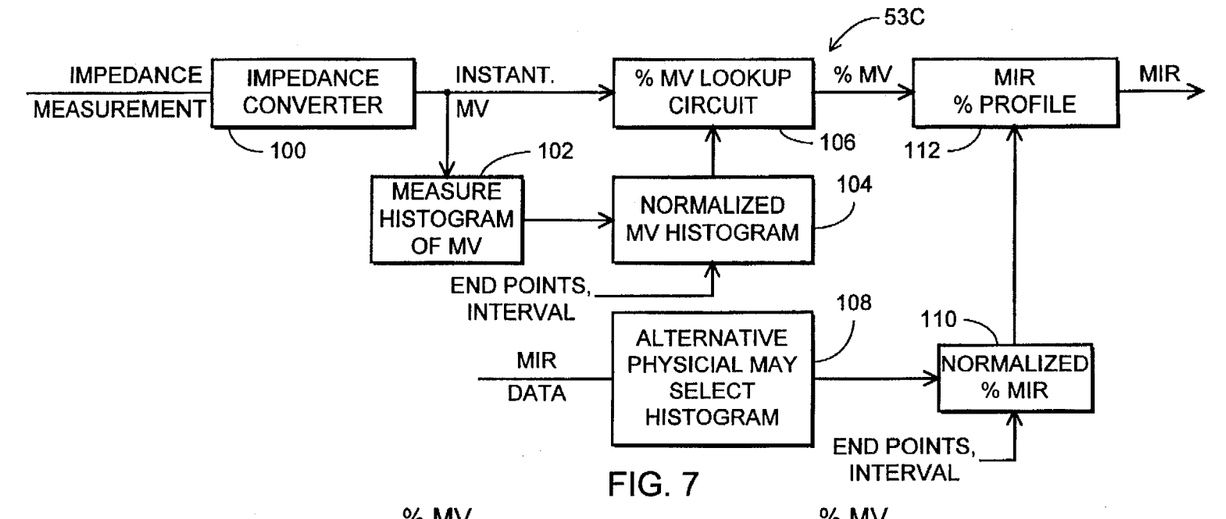
FIG. 7 shows a block diagram of the minute volume processor of FIG. 4.
Figure 8A:
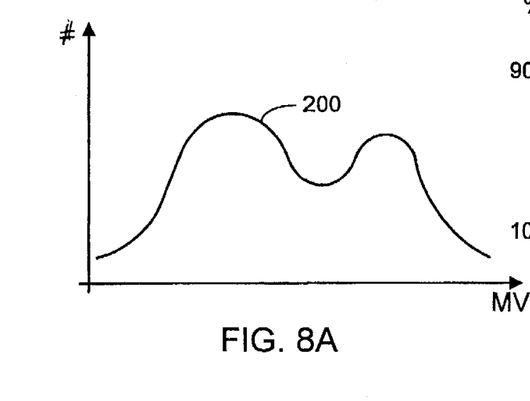
FIG. 8a shows a typical MV distribution curve.
Figure 8B:
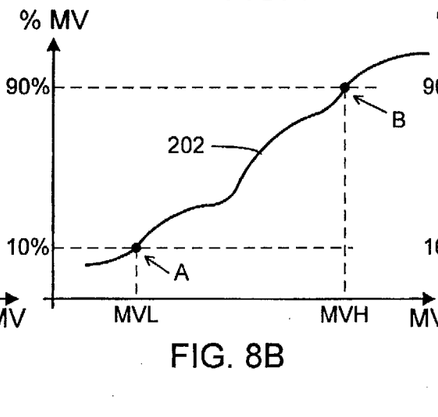

An important feature of the invention is the manner in which the minute volume processor 53A operates to determine the optimal metabolic indicated rate (MIR) from the instantaneous minute volume. As shown in more detail in FIG. 7, the minute volume processor 53A includes an impedance converter 100 which converts the impedance measurement received from circuit 41 (FIG. 2) into a corresponding instantaneous minute volume parameter (MV), as described fore example in U.S. Pat. No. 4,901,725. This parameter is monitored for a relatively long time period, extending for example from two weeks to several months to generate a histogram by a histogram generator 102. The histogram generator 102 may be formed, for example, of a plurality of counters, each counter being incremented when an MV in a particular range is detected. This histogram is fed to an MV normalizing circuit 104. This circuit also receives as its input the desired end points, or one of the end points and the interval between end points which define the normalization. These normalizing parameters may be preprogrammed, or may be selected by a physician. For example, FIG. 8a shows a typical distribution curve 200 that may be obtained for a patient over a prolonged period of time. FIG. 8b shows the integral curve 202 of the curve 200 as explained more fully in U.S. Pat. No. 4,856,522. Importantly rather than using the curve 202, the normalize M circuit 104 performs normalizing or linearizing function as follows. Based on data obtained in the past, the desired shape of the optimal curve is selected. For example this curve may be linear between a lower and an upper limit MVL and MVH of MV corresponding, for example to the 10% and the 90% percentile points, respectively. It should be understood that other points may be selected as well. These end points then A(LMV, 10%) and B(HMV, 90%) are used to define a new normalized curve 204 shown in FIG. 8c. As seen in this Figure, curve 204 is linear between its end points A, B. It should be understood that other shaped curve may be used as well. Below A and above B curve 204 follows curve 202.

Figure 8C:
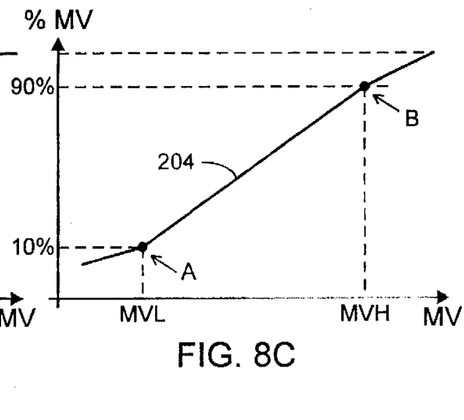
FIG. 8c shows the curve of FIG. 8b normalized in accordance with this invention.

This curve 204 is fed to a look up circuit 106. The look-up circuit receives the instantaneous MV from circuit 100 and using the curve 204 as a profile, generates a corresponding % MV profile.

An MIR histogram is stored in histogram generator 108, preferably when the pacemaker is initially programmed. Alternatively, the physician may define the histogram at will, based, for example, on his past experience, published cardiac data, etc. The MIR histogram is illustrated by curve 300 in FIG. 9a.

Figures 9A, 9B, 9C:
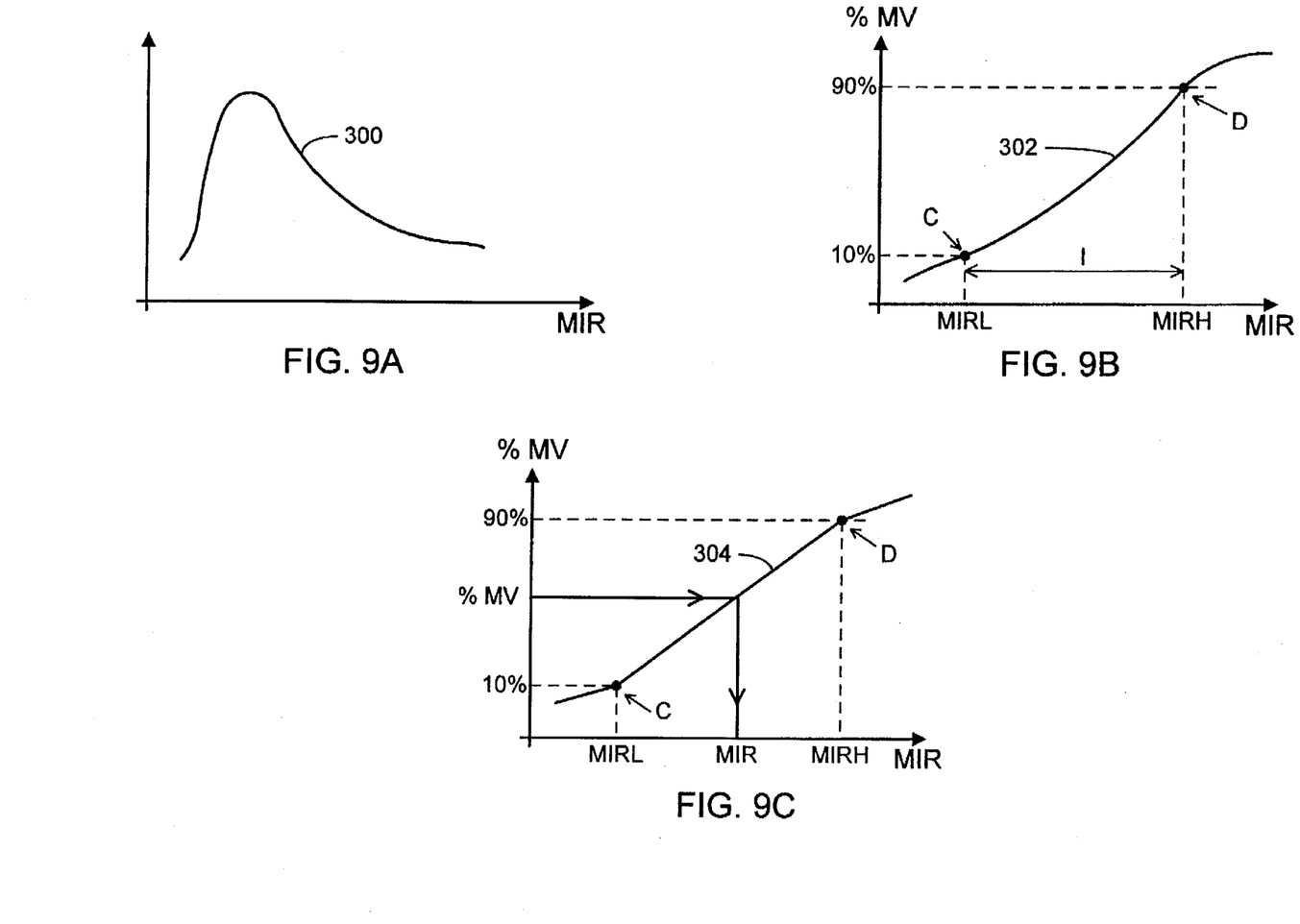

The MIR histogram is integrated and normalized by circuit 110. More particularly, first curve 302 is generated by integrating curve 300 (FIG. 9b). Next, two end points C and D are selected based on preselected criteria, such for example by defining the points C (MIRL, 10%) and D (MIRH, 90%). Alternatively, point C may be defined by its coordinates, and point D may be defined as being a predetermined interval I higher than MIRL. These two end points C and D are again used to generate a profile curve 304, wherein at least between points C and D the curve 304 is linear or has any other desired shape (FIG. 9c). Below C and above D curve curve 304 follows curve 302. Curve 304 is provided to a second look up table 112 as an MIR percentile profile. Importantly, the curve 304 is calculated a priori before the pacemaker is operational. Therefore, the calculations for determining curve 304 can be performed either in the pacemaker or in an external programmer, in which care the MIR histogram generator 108 and/or the normalizing circuit 110 can be external. Again, while curve 304 is defined as being linear between points C and D, it may have other shapes as well.

The % MV from table 106 is used now to look up a corresponding rate MIR using curve 304.

In this manner the physician is given the freedom of choosing the distribution curve for the MV (204) or the MIR (304) or both.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. An implantable pacemaker comprising:

a pacing pulse generator for generating pacing pulses in accordance with a control signal;

a cardiac sensor for sensing intrinsic cardiac beats and for generating corresponding sensed signals;

a metabolic sensor for sensing a metabolic demand and for generating a corresponding metabolic demand signal; and a controller for generating said control signal responsive to said sensed signal and said metabolic demand signal;

wherein said metabolic sensor includes a histogram generator for generating an initial histogram for said metabolic demand, said initial histogram having a first initial portion and a second initial portion, and a normalized histogram, said normalized histogram including said first initial portion and a normalized portion, a normalizer for generating said normalized portion by normalizing said second initial portion in accordance with a preselected criteria, and a demand rate generator for generating said demand rate from said normalized histogram.

2. The pacemaker of claim 1 wherein said metabolic sensor includes a memory for holding a metabolic rate profile, and a metabolic rate selector for selecting said metabolic rate from an instantaneous demand rate in accordance with said profile.

3. A rate responsive implantable pacemaker comprising:

a rate control parameter generator for generating a rate control parameter;

a pulse generator for generating pacing pulses on demand in accordance with a rate control signal; and a controller including a histogram generator for generating an initial histogram including a first initial histogram portion and a second initial histogram portion for said rate control parameter, a normalizer for generating a normalized histogram from said initial histogram, said normalized histogram including said first initial histogram portion for a first rate range and a normalized histogram portion for a second rate range, said normalized histogram portion having predetermined characteristics, and a selector for selecting said rate control signal in accordance with said normalized histogram in response to an instantaneous rate control parameter, wherein said rate control signal is determined by said initial histogram portion when said instantaneous rate control parameter corresponds to said first rate range and wherein said rate control signal is determined by said normalized histogram portion when said instantaneous rate control parameter corresponds to said second rate range.

4. The pacemaker of claim 3 wherein said controller further comprises a memory for holding a rate control profile, said selector generating said rate control signal from said rate control profile.

5. The pacemaker of claim 4 wherein said rate control profile is normalized from a rate control signal histogram.

6. The pacemaker of claim 3 further comprising a metabolic demand rate generator for generating a metabolic demand rate dependent on a patient's metabolic demand.

7. The pacemaker of claim 6 wherein said metabolic demand rate generator includes an impedance generator for generating a transthoracic impedance indicative of said metabolic demand.

8. The pacemaker of claim 3 wherein said second range is defined between a lower and an upper limit and wherein said first range is below said lower or above said upper limit.

9. The pacemaker of claim 8 wherein said lower and upper limits are predetermined parameters.

10. A method of generating pacing pulses on demand for a patient using an implantable pacemaker, said method comprising the steps of:

generating a rate control parameter;

generating an initial parameter histogram for said rate control parameter over an extended time period of at least a day, said initial parameter histogram including a first initial histogram portion and a second initial histogram portion;

converting said initial parameter histogram into a normalized parameter histogram having predetermined characteristics, said normalized parameter histogram including a first normalized histogram portion corresponding to said first initial histogram portion and a second normalized histogram portion generated by normalizing said second initial histogram portion;

selecting a control rate based on said normalized parameter histogram using an instantaneous rate parameter, wherein said control rate is selected using said first normalized histogram portion for a first range of said instantaneous rate parameter and wherein said control rate is selected using said second normalized histogram portion for a second rate of said instantaneous rate; and generating demand pacing pulses at said control rate.

11. The method of claim 10 further comprising the step of generating a control rate profile and mapping said normalized histogram to said profile.

12. The method of claim 11 further comprising the step of generating an initial control rate histogram, and converting said initial control rate histogram into a normalized control rate histogram, said control rate histogram having predetermined characteristics.

13. The method of claim 12 further determining an instantaneous metabolic demand parameter, said control parameter being indicative of said instantaneous metabolic demand.

14. The method of claim 13 further comprising determining a transthoracic impedance for said patient, said transthoracic impedance being indicative of metabolic demand.

15. An implantable pacemaker comprising:

a pacing pulse generator for generating pacing pulses in accordance with a control signal;

a cardiac sensor for sensing intrinsic cardiac beats and for generating corresponding sensed signals;

a metabolic sensor for sensing a metabolic demand and for generating a corresponding metabolic demand signal; and a controller for generating said control signal responsive to said sensed signal and said metabolic demand signal;

a histogram generator for generating an initial demand histogram for said metabolic demand, an initial sensor histogram for said cardiac beats and a normalized histogram derived from one of said initial histograms in accordance with a preselected criteria, said normalized histogram including a portion of said one initial histogram, and a normalized histogram portion , and a demand generator for generating said demand rate from said normalized histogram.

16. The pacemaker of claim 15 further comprising a memory holding a profile defined by said normalized histogram, said profile relating each specific metabolic demand to a specific metabolic demand rate.

17. The pacemaker of claim 16 wherein said profile includes a normalized profile portion dependent on said initial histograms and normalized profile portion dependent on said normalized histogram.

* * * * *